United States Patent [19]

Roscher et al.

[11] Patent Number: 5,319,138
[45] Date of Patent: Jun. 7, 1994

[54] PROCESS FOR THE PREPARATION OF PURE PROPANEPHOSPHONIC ANHYDRIDE

[75] Inventors: Günter Roscher, Kelkheim; Hans-Jerg Kleiner, Kronberg/Taunus; Harald Berger; Manfred Schmidt, both of Kelkheim; Rainer Uhmann, Kriftel/Taunus; Dirk Böttger, Hünstetten, all of Fed. Rep. of Germany

[73] Assignee: Hoechst Aktiengesellschaft, Frankfurt, Fed. Rep. of Germany

[21] Appl. No.: 926,495

[22] Filed: Aug. 5, 1992

[30] Foreign Application Priority Data

Aug. 8, 1991 [DE] Fed. Rep. of Germany ....... 4126235

[51] Int. Cl.$^5$ .............................................. C07F 9/30
[52] U.S. Cl. ................................................... 562/878
[58] Field of Search ........................................ 562/878

[56] References Cited

U.S. PATENT DOCUMENTS

| | | | |
|---|---|---|---|
| 4,195,035 | 4/1980 | Kleiner et al. | 562/878 |
| 4,267,125 | 5/1981 | Dürsch et al. | 562/878 |
| 4,331,592 | 5/1982 | Wissmann et al. | 530/342 |

FOREIGN PATENT DOCUMENTS 2758580  7/1979  Fed. Rep. of Germany.
2811628  9/1979  Fed. Rep. of Germany.

OTHER PUBLICATIONS

Derwent Abstract of German laid-open application 27 58 580, Jul. 1979.

Primary Examiner—José G. Dees
Assistant Examiner—Dwayne C. Jones
Attorney, Agent, or Firm—Connolly & Hutz

[57] ABSTRACT

Process for the preparation of pure propanephosphonic anhydride, which comprises distilling crude, impure propanephosphonic anhydride having an average degree of polymerization of 20 to 200 and containing less than 0.5% by weight of water by heating to 230 to 300° C. under a pressure of 0.1 to 100 mbar, pure propanephosphonic anhydride having an average degree of polymerization of 20 to 60 being obtained.

7 Claims, No Drawings

PROCESS FOR THE PREPARATION OF PURE PROPANEPHOSPHONIC ANHYDRIDE

FIELD OF THE INVENTION

The invention relates to a process for the preparation of pure propanephosphonic anhydride by distillation.

BACKGROUND OF THE INVENTION

Propanephosphonic anhydride is a valuable intermediate product. It is used, for example, for the preparation of flameproofing agents, for corrosion prevention on metals, for formation of complexes with metals, for linking peptides or as a crosslinking agent for polymers. For many of the intended uses mentioned, it is necessary to employ propanephosphonic anhydride which is as far as possible colorless and pure. This means that the propanephosphonic anhydride must in general contain 95% by weight, but at least more than 85% by weight, of the component mentioned, and the remainder should not contain intensely colored impurities. The propanephosphonic anhydride is not a compound of defined molecular size, i.e. defined degree of polymerization, but a mixture of polymolecular anhydrides of different chain length formed by elimination of water from the propanephosphonic acid groups, it also being possible for cyclic anhydrides to be present.

Various methods are known for the preparation of alkanephosphonic acid anhydrides. Those processes which start from phosphonic acids are of particular interest here. It is known first to convert the phosphonic acids into phosphonyl dichloride using phosphorus trichloride, thionyl chloride or phosgene, and then to purify the low-boiling propanephosphonyl dichloride by distillation. This product is then reacted with the stoichiometric amount of water or with propanephosphonic acid to give propanephosphonic anhydride and hydrogen chloride. Because of the use of chlorinating agents and of the hydrogen chloride unavoidably obtained, this method meets technical difficulties.

U.S. Pat. No. 4,195,035 describes in Example 2 a process for preparing propanephosphonic anhydride by heating propanephosphonic acid at 360°–420° C. under a pressure of 25 mm Hg. This eventually results in the elimination of water, which is distilled off together with the low molecular weight propanephosphonic anhydride formed by the elimination of water. This process can be realized industrially only with difficulty and with great expense. Practically no apparatus material is resistant in the long term at the high temperature required for elimination of the water, because of the corrosive aggressiveness of the medium. Furthermore, when the propanephosphonic anhydride which distills over together with the eliminated water is condensed in the condensation step, some of the propanephosphonic anhydride formed unavoidably reacts again with the gaseous eliminated water, so that the propanephosphonic anhydride formed always contains portions of re-formed propanephosphonic acid. The propanephosphonic anhydride which is formed in the first stage and distills over together with the eliminated water probably comprises cyclic, low molecular weight compounds. This process moreover requires the use of relatively pure propanephosphonic acid, because by-products contained therein also distill at the high temperatures necessary for elimination of the water, and therefore contaminate the resulting propanephosphonic anhydride.

The present invention now provides a process for the preparation of pure propanephosphonic anhydride in which the disadvantages mentioned for the customary processes no longer occur.

It has now been found that impure polymolecular propanephosphonic anhydride can be distilled under certain conditions as low molecular weight cyclic propanephosphonic anhydride, which changes back into higher molecular weight purified propanephosphonic anhydride when the vapors condense.

DESCRIPTION OF THE INVENTION

The invention therefore relates to a process for the preparation of pure propanephosphonic anhydride, which comprises distilling crude, impure propanephosphonic anhydride having an average degree of polymerization of 20 to 200 and comprising less than 0.5% by weight of water by heating at 230° to 300° C. under a pressure of 0.1 to 100 mbar, propanephosphonic anhydride having an average degree of polymerization of 20 to 60, preferably 25 to 40, being obtained.

The propanephosphonic anhydride purified in this way is obtained as a colorless distillate in a purity of more than 90 to 95% by weight.

The process according to the invention is preferably carried out at temperatures from 250° to 290° C., in particular from 260° to 280° C., under pressures of preferably 1 to 30 mbar.

The water content of the crude propanephosphonic anhydride is in general less than 0.2% by weight, in particular less than 0.1% by weight.

In a preferred embodiment, the crude propanephosphonic anhydride employed is one such as is obtained by the process of DE-OS 2,758,580. In this process, propanephosphonic acid is transanhydrized with acetic anhydride. However, the crude propanephosphonic anhydride can also be prepared by any other customary process.

It is particularly surprising that polymolecular propanephosphonic anhydride, which cannot be distilled and is very heat-stable, forms, on heating under the conditions according to the invention, distillable low molecular weight cyclic propanephosphonic anhydride, which changes back, however, into higher molecular weight propanephosphonic anhydride when the vapors condense. The fact that depolymerization to give distillable low molecular weight units was not to be expected can also be seen from page 12 of DE-OS 2,758,580, according to which dark-colored anhydrides can be used if, after their chemical reaction, the secondary products formed are distillable.

EXAMPLES 1. 70 kg of 90% strength propanephosphonic acid having a water content of more than 0.5% and 275 kg of acetic anhydride are initially introduced into a 400 l enamel stirred kettle with steam heating in a jacket and an attached glass column (diameter 100 mm, length 4 m, packing 12 mm glass spirals) with an automatic reflux divider, distillate receivers, cold trap and vacuum connection. After heating the mixture to the boiling point, 70 kg of acetic acid containing less than 5% acetic anhydride are distilled off at a reflux ratio of 8. The internal temperature of the kettle is then increased to 150° C. and the reflux ratio is reduced to 1. When a bottom temperature of 150° C. is reached, the pressure is reduced successively, until no further distillate is obtained at an internal temperature of the kettle of 150° C. and a pressure of 10 mbar. Together with the product in the cold trap, a total of 200 kg of distillate are obtained. This contains more than 90% of acetic anhydride and less than 10% of acetic acid. 67 kg of crude propanephosphonic anhydride remain as the residue. This strongly dark-colored polymeric propanephosphonic anhydride having a degree of polymerization of 20 to 200 is 76% pure according to the P-NMR. The propanephosphonic acid content is 4%. The remainder comprises secondary components which have not been clarified by analysis and cause the heavy coloration.

40 kg of the crude, strongly dark-colored propanephosphonic anhydride having a water content of less than 0.05% were initially introduced into a 50 l ®Hastelloy stirred kettle with a jacket, which was heated by heat transfer oil in forced circulation, condenser with a distillate receiver and vacuum connection. After a reduced pressure of 10 mbar had been applied, the contents of the kettle were heated. At an internal temperature of the kettle of 270° C., 30 kg of colorless distillate, which solidified at room temperature, were obtained in the distillate receiver. According to phosphorus-NMR analysis, the distillate contained 95% by weight of propanephosphonic anhydride with an average degree of polymerization of about 30. The distillation time was 1 hour.

2. The procedure was as in Example 1, except that propanephosphonic acid which was only about 65% pure and contained relatively large amounts of various phosphonic acids, in addition to undefined compounds, was employed to prepare the crude propanephosphonic anhydride. The tarry crude propanephosphonic anhydride which was obtained by transanhydridation with acetic anhydride and had a water content of less than 0.05% and an average degree of polymerization of 150 was 58% pure according to phosphorus-NMR analysis. Under the conditions of Example 1, 24.5 kg of colorless distillate which, according to phosphorus-NMR analysis, contained 91% by weight of propanephosphonic anhydride having an average degree of polymerization of about 30 were obtained from 40 kg of crude anhydride.

COMPARISON EXAMPLE

The kettle heating in the jacket of the Hastelloy stirred kettle was changed from normal heat transfer oil, the temperature range of which extends up to 300° C., to ®Diphyl and was operated under increased pressure so that internal temperatures in the kettle of more than 300° C. can be achieved.

40 kg of 90% pure propanephosphonic acid which was strongly colored was introduced into the kettle. After a reduced pressure of 10 mbar had been applied, the contents of the kettle were heated up, and at an internal temperature of the kettle of 340° C. distillates started to be obtained. After 5 hours, no further distillate was obtained. The total amount of distillate was 28 kg. According to phosphorus-NMR analysis, the yellow-colored distillate contained 55% by weight of propanephosphonic anhydride and 33% by weight of propanephosphonic acid.

We claim:

1. A process for the preparation of pure propanephosphonic anhydride, which comprises distilling crude, impure propanephosphonic anhydride having an average degree of polymerization of 20 to 200 and comprising less than 0.5% by weight of water by heating at 230° to 300° C. under a pressure of 0.1 to 100 mbar, pure propanephosphonic anhydride having an average degree of polymerization of 20 to 60 being obtained.

2. A process as claimed in claim 1, wherein the crude, impure propanephosphonic anhydride is obtained by transanhydration of propanephosphonic acid with acetic anhydride.

3. The process as claimed in claim 1, wherein the water content in the crude propanephosphonic anhydride is less than 0.2% by weight.

4. The process as claimed in claim 1, wherein the water content in the crude propanephosphonic anhydride is less than 0.1% by weight.

5. The process as claimed in claim 1, wherein the process is carried out at temperatures from 250° to 290° C.

6. The process as claimed in claim 1, wherein the process is carried out at temperatures from 260° to 280° C.

7. The process as claimed in claim 1, wherein the process is carried out under a pressure of 1 to 30 mbar.

* * * * *